ns patent [19]

Ivani

[11] 4,365,050
[45] Dec. 21, 1982

[54] AMINO-POLYSACCHARIDES AND COPOLYMERS THEREOF FOR CONTACT LENSES AND OPHTHALMIC COMPOSITIONS

[76] Inventor: Edward J. Ivani, 2360 E. 74 St., Brooklyn, N.Y. 11234

[21] Appl. No.: 283,613

[22] Filed: Jul. 15, 1981

[51] Int. Cl.³ .................... C08L 5/08; C08L 89/00
[52] U.S. Cl. .................................... 527/312; 523/106; 523/107; 523/108; 525/8; 525/54.1; 525/54.3; 525/937; 527/100; 527/102; 527/201; 527/300; 527/313; 527/314; 527/315; 528/10; 528/25; 528/33; 536/20; 536/53; 536/55.1; 260/112 R; 260/112 G

[58] Field of Search ............... 523/106, 107, 108; 525/8, 50, 54.1, 54.2, 54.3, 54.32, 937; 527/100, 101, 102, 201, 203, 300, 312, 313, 314, 315; 528/10, 25, 33; 536/18, 20; 260/112 R, 112 G

[56] References Cited

U.S. PATENT DOCUMENTS 3,332,897 7/1967 Ray-Chaudhuri ............... 527/312
3,770,673 11/1973 Slagel et al. .................... 527/312
4,264,155 4/1981 Miyata ............................ 523/106

*Primary Examiner*—John Kight, III
*Assistant Examiner*—Nathan M. Nutter
*Attorney, Agent, or Firm*—Abelman, Frayne & Rezac

[57] ABSTRACT

Aminopolysaccharides and copolymers thereof, primarily those of N-acetyl-D-glucosamines and derivatives and various monomers, is described.

7 Claims, No Drawings

AMINO-POLYSACCHARIDES AND COPOLYMERS THEREOF FOR CONTACT LENSES AND OPHTHALMIC COMPOSITIONS

BACKGROUND OF THE INVENTION

This invention relates to the use of a polysaccharide known as chitin, as well as other derivatives of chitin, and copolymers of the family of materials known as amino-polysaccharides useful for making contact lenses or parts thereof, artificial corneas and interocular lens types, drug delivery systems, vaginal spermicides and creams, injectable encapsulation materials and other medical devices and pharmaceuticals. These amino-polysaccharides are used alone or as components in a polymeric arrangement, such as polymer blends, graft or block copolymers, or any other combination of modified compositions.

Chitin is an amino sugar, in which one or more of the hydroxyl groups of the carbohydrate are replaced by an amino group. Chitin is one of the most abundant amino sugar derivatives. The amino polysaccharide is made up of 2-acetamido-2-deoxyglucose units linked in a B-1,4 manner similar to that in cellulose, or starch, or in general it is indicated as N-acetyl-D-gluocosamine, and is found as a structural material in the invertebrate animal world. The exoskeletons of insects and crustaceans contain large amounts of this amino polysaccharide. The observation of the exoskeleton of shrimp and other invertebrates indicates that this material can be made clear, flexible, hard, and permeable, which would be useful for medical devices.

Chitin has been estimated to be the second most abundant polysaccharide in nature with synthesis in the neighborhood of a billion tons a year. However, in the natural state it occurs in small flakes or as short fibrous materials, and is not capable of forming useful shaped articles without solution and reprecipitation or renaturing. Methods of dissolving chitin in certain solvents are described in the literature. For example, Clarke and Smith, J. Phys. Chem., 40, 863 (1936), use aqueous acids or lithium salts for solution and regeneration of chitin. These authors observed the formation of addition compounds of chitin with lithium thiocyanate and with sodium hydroxide under certain conditions. However, the formation of addition compounds or complexes of chitin with organic compounds has not been described.

The N-acetyl-D-glucosamine can be prepared in 60 to 70% yields by the hydrolysis of the exoskeleton of crustaceans with concentrated hydrochloric acid;

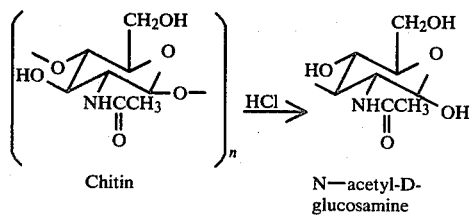

Chitin    N—acetyl-D-glucosamine

Poly(N-acetyl-D-glucosamine) is a major component of naturally occurring chitin. The naturally occurring material has not only the poly(N-acetyl-D-glucosamine) but also inorganic salts thought to be forms of calcium carbonate and proteinaceous materials, the composition of which is not presently known. The term N-acetyl-D-glucosamine is used herein to refer to the various naturally occurring forms of chitin including the purified and or naturally occurring form. A method of extracting the N-acetyl-D-glucosamine is the following: chitin is finely ground in a ball mill overnight or until it passes a 6 mm screen and can be retained by a 1 mm screen. 149 g of this finely ground material is decalcified by extracting with 825 ml of 2 N HCl at 4° C. for 48 hours in a flask stirred with a magnetic stirrer. The material is collected by centrifugation and washed repeatedly with water until neutral. The ash content is about 0.4–0.5%. The decalcified chitin is then stirred at room temperature with 1500 ml of 90% formic acid overnight. The mixture is centrifuged and the residue repeatedly washed with water. The washed chitin is then suspended in 2 liters of 10% NaOH solution and heated at 90°–100° C. for 2.5 hours. The solution is filtered, and washed with water until neutral, washed several times with absolute ethanol and ether, and dried at 40° C. under reduced pressure to yield poly(N-acetyl-D-glucosamine).

PRIOR ART

Carboxymethylchitin is disclosed in Carbohyd. Res. 7, 483–485 (1968), R. Trujillo. This article mentions the hydrolysis of both chitin and carboxymethylchitin by lysozyme.

U.S. Pat. No. 3,632,754 teaches the application of a powder or solution of chitin or chitin derivative to accelerate the rate of wound healing in mammals.

U.S. Pat. No. 4,063,016 teaches compositions of chitin with lower molecular weight alcohols, aldehydes and ketones.

U.S. Pat. No. 3,892,731 teaches the use of di-or-trichloroacetic acid as a solvent for chitin.

U.S. Pat. No. 4,027,068 describes a method of using chitin derivatives as defoggers for clear surfaces and as deodorizers.

U.S. Pat. No. 3,988,411 teaches that poly(N-acetyl-D-glucosamine) is soluble in hexafluoroisopropyl alcohol and hexafluoroacetone sesquihydrate.

U.S. Pat. No. 3,847,897 teaches how to prepare microcrystalline chitin by subjecting chitin to controlled acid hydrolysis and high shear while suspended in aqueous medium.

SUMMARY OF THE INVENTION

It is the essence of this invention to utilize the unique properties of N-acetyl-glucosamine, substituted D-glucosamine, and copolymers of D-glucosamine, in an area of application which can take advantage of the properties of these materials, that being the ophthalmic field of contact lenses, ophthalmic drug preparations, contact lens solutions, etc.

It is interesting to note other structural amino polysaccharides which can be used in this invention. Hyaluronic acid is an amino polysaccharide of 2-amino-2-deoxyglucose and glucuronic acid. This polymer polysaccharide is an important component of animal connective tissue and of the synovial fluid which is the natural lubricant of joints. 2-amino-deoxygalactose, is also an important naturally occurring amino acid known for many years as a component of the polysaccharide chondroitin sulfate. This polymer is among the principal polysaccharides of cartilage and is structurally similar to hyaluronic acid, except that the amino sugar is galactose instead of glucose and a sulfate group is also present. The reactions with N-acetyl-D-glucosamine and the above amino polysaccharides are similar, and with slight modifications of the methods can be substituted for N-acetyl-D-glucosamine.

There are similarities between the amino-polysaccharides, and starch and cellulose. All have hydroxyl groups which may be esterified by inorganic or organic acids to modify their properties. The literature shows the formation of a complex of chitin with an oxygen-containing complexing agent containing up to 10 carbon atoms selected from the group consisting of saturated aliphatic and alicyclic alcohols, aldehydes, and ketones. It is possible to prepare derivatives which have more than one type of substituent on the chitin chain. Derivatives of chitin can be formed by attaching a substituent to the 6-hydroxyl oxygen or by removing the N-acetyl group to form chitosan, and attaching another substituent to the nitrogen. Chitosan itself is commercially available, and is thus a useful starting material for the preparation of chitin derivatives in which a substituent is attached to the nitrogen. The carboxy-containing chitin derivatives which are useful are the O-carboxyalkyl chitin, in which a carboxy alkyl group is attached to the 6-hydroxyl oxygen through the alkyl group; N-carboxyalkyl chitosans in which a carboxyalkyl group is attached to the nitrogen through the alkyl group, and N-carboxyacyl chitosan in which the nitrogen is acylated with material containing a carboxyl group in addition to the acyl group which is attached to the nitrogen. Substituents need not be limited to one type of substituent on the chitin chain. These other substituents need not be limited to carboxy containing substituents, and in fact, alkyl and substituted alkyl substituents having 2-18 C-atoms are often used because they can modify the solubility of the chitin derivatives.

Some of the substituted N-acetyl-D-glucosamines can be used in an enzymatically degradable form by the selection of specific substituents. Examples of these are poly(M-acetyl-6-O-(carboxymethyl)-D-glucosamine), poly(N-acetyl-6-O-(2-hydroxyethyl)-D-glucosamine) and poly (N-acetyl-6-O-(ethyl)-D-glucosamine).

To form poly(N-acetyl-6-O-(2-hydroxyethyl)-D-glucosamine), 13.6 g of purified poly (N-acetyl-D-glucosamine) milled so that it passes a 1 mm sieve are placed in a screw-cap bottle. Then 200 ml of cold (0°-5° C.) aqueous 43% NaOH are added and the contents stirred for two hours under nitrogen and then hold at 0°-4° C. for 10 hours. The swollen alkali derivative is then squeezed to 3 times its original weight in a sintered glass funnel, disintegrated and frozen at −20° C. under nitrogen for one hour and then thawed at room temperature for one hour. The freeze/thaw cycle is repeated 3 times. To the alkali derivative are added 120 ml of dimethyl sulfoxide and the slurry is immediately stirred and autoclayed. The autoclave is purged several times with nitrogen and 53.2 ml of ethylene oxide are added. The mixture is held at 50° C. for 18 hours. The solution is carefully neutralized with glacial acetic acid. The alkyl-substituted N-acetyl-D-glucosamine can be cross-linked by forming an aqueous solution with acetone and using an olefin glycol dimethacrylate such as ethylene glycol dimethacrylate, etc. This will add to the tensile strength of the film formed.

The ability to modify chitin by substituents, allows for the material to be substituted, or compounded, using bio-organic compounds which can modify its properties for use in medical devices. Some of the bio-organic compounds which can be added by substitution, block and grafting, or polyblending, are collagen, which has a composition in which one-third of the amino acid residues are glycine; elastin and resilin may also be used. Resilin is insoluble in the usual solvents and in solutions of urea, these can reduce the enzymatic reaction of the body on some of the compounds of N-acetyl-D-glucosamine, and can regulate the biodegradability of the material in certain uses.

To prepare a collagen derivative of chitin, or chitosan, 3.44 gms in a solution, which yield 4% chitosan, in 2% acetic acid (vacuum filtered), 3.44 gms of 8% Crotein SPC in 2% acetic acid, and 0.033 of 0.593% glutaraldehyde. The mixture is heated at 60° for about 4 hours to encourage interaction. The solution is evaporated by heating to 100° C. for approximately 4 hours. The residual product is evaporated and dried at 80° C. The materials are hard and brittle, but become pliable after soaking in water. The D-glucosamine-collagen complex forms a clear polymer which can be used internally as an enzymatic degradable drug delivery system, vaginal cream and spermicide, etc.

For the following discussion the term D-glucosamine will be used for N-acetyl-D-glucosamine, poly(N-acetyl-D-glucosamine), and any of its derivatives, or substituted derivatives.

To alter the physical properties of the D-glucosamine, it may be graft or block copolymerized with known polymers to alter its chemical structure. In order to form graft or block copolymers with D-glucosamine it will be necessary to form free radicals. In free radical-initiated graft copolymerization, a free radical produced on the D-glucosamine reacts with a monomer to form graft copolymers. A number of initiating methods are used to prepare graft copolymers, initiation by chemical methods and initiation by irradiation. The method of choice depends on the monomer to be copolymerized, the substitution on the D-glucosamine etc. a little thought will determine the appropriate procedure; it is the final copolymers which have the desired biomedical use and not the specific pathway to achieve them. The copolymer graft composition of this invention beside the biopolymers, consist essentially of the D-glucosamine units of the indicated reaction formulae, and any acrylonitrile, acrylamide, alkyl methacrylate. The acetate, propionate, and butyrate esters of the D-glucosamine-g-poly(ethyl acrylate) and D-glucosamine-g-poly(butyl acrylate) copolymers can readily be formed. This graft polymerization reaction can be performed either in solution, emulsion or suspension. A part or whole of the redox catalyst in the reaction mixture may be replaced by a peroxide catalyst or a diazo compound catalyst. Free radicals have been formed on polyglucoses by chain transfer reactions. A frequently used method is the reaction of a polysaccharide with hydrogen peroxide in the presence of a ferrous salt, such as ferrous ammonium sulphate. Hydroxyl radicals are produced from the hydrogen peroxide-ferrous ion system, and these free radicals then abstract hydrogen atoms from the polysaccharide. Hydrogen peroxide has been replaced by organic hydroperoxides or inorganic persulfate salts, and such reducing agents as sodium bisulphite have been substituted for ferrous ion. Mixtures of ferrous ammonium sulphate and ascorbic acid can also serve as the reducing portion of the redox system. The use of the catalyst compounds, may be omitted, under certain conditions and the materials heat polymerized under suspending or emulsifying conditions. Or the use of catalyst compounds may be omitted, and ozone introduced into an aqueous solution of D-glucosamine, after which the reaction system is heated and the oxidized D-glucosamine is graft polymerized with either an alkyl methacrylate, acrylonitrile, or an acrylamide under suspending or emulsifying conditions. Where graft polymerization is carried out using a redox catalyst, a solution polymerization may be employed using a solvent which can dissolve both the D-glucosamine and the copolymer, or a combination of solvents can be used. The materials may be polymerized in emulsion in the presence of a basic, neutral or acidic surface active agent in an aqueous medium. Or it can be polymerized in suspension by omitting the use of a surfactant. The presence of molecular oxygen reduces the activity of the redox catalyst and therefore, the reaction should be carried out after purging the liquid reaction medium and reaction zone with nitrogen. Furthermore, a compound capable of forming the copolymer compounds under acidic conditions during the polymerization reaction, such as cerium hydroxide, can be used.

The following is a method of initiating free radicals on the D-glucosamine. The method involves the use of ceric salts, such as ceric ammonium nitrate dissolved in nitric acid. The method is used to graft copolymerize a number of monomers onto both starch and cellulose polysaccharides. Based on available information the most likely reaction path for ceric grafted copolymerization would appear to be:

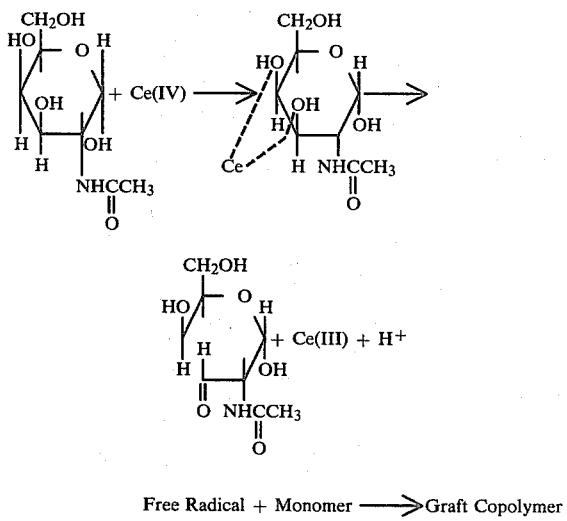

Free Radical + Monomer ⟶ Graft Copolymer

After initial formation of a D-glucosamine ceric complex, ceric ion is reduced to cerous, a hydrogen atom is oxidized, and a free radical is formed on the D-glucosamine. The free radical D-glucosamine formed may then react with monomer to initiate graft copolymers. The reaction with the formed free radicals allows for the formation of the following compounds: D-glucosamine-acrylonitrile with varying degrees of substitution of the acrylonitrile onto the D-glucosamine to vary the characteristics of the material. The formation of D-glucosamine and acrylamides, such as diacetone acrylamide, ethylacrylamide; N,N diethylacrylamide, etc. The acrylic acids and esters, and the modified acrylic acids and esters, as well as the methacrylates can be used.

The formation of copolymers of chitin and chitin derivatives with silicones produces a class of copolymers which will find extensive use in biomedicine and bioengineering.

The basic structure of the silicones is exhibited by polydimethylsiloxanes. A variety of groups can be substituted for the methyl group in a silicone, among some of the substitute groups are $C_6H_5$-phenyl, $CF_3CH_2CH_2$-trifluoropropyl, H-hydride which introduces metal catalyzed and vinyl-addition cross-link sites, HO-silanol cross linking points for condensation and metal-catalyzed cross-linking, $CH_2=CH$-vinyl increases peroxide reactivity, and introduces cross-link points for vinyl addition.

Since some of the properties of the silicone homopolymers are not totally compatable with biological use, the modified N-glucosamine-silicone will find increased biological use because of the unique wetting properties, hydrophilic nature, of the chitosan and other N-glucosamine derivatives. These hydrophilic properties will impart sufficient wettability to the silicone to reduce tissue reaction with these materials, which may be formed into implant devices, contact lenses, etc.

The chemistry of the silicones is well defined and bridge polymer links between the silicone and chitin complexes are possible, as in the transition between the siloxane to a carbinol-terminated (C—OH) polymer, which can be reacted with isocyanetes to form a urethane linkage. Urethane linkage can be created by reacting silanol-terminated polymers with ethylene oxide to yield ethanol ether ($SiOCH_2CH_2OH$), by hydrating vinyl-terminated polymers ($SiCH_2CH_2OH$) and by adding allyl alcohol to hydride terminated polymers ($SiCH_2CH_2$—$CH_2OH$).

Several silicone materials have been tried for use in contact lenses because of the enhance oxygen permeability of the silicone, however, a variety of mechanical, optical, and wetting requirements posed a considerable problem to bioengineers. By copolymerizing the silicone with a N-glucosamine many of the problems, and in particular the non-wetting characteristics can be eliminated. This modified silicone-N-glucosamine complex can find many uses in biomedicine besides contact lenses, some of the uses are given in this disclosure, others will become possible by those skilled in the art.

Since extensive work has been done with the polysaccharide starch, and the D-glucosamine is structurally similar to starch, the block and graft copolymers possible with starch should be possible with D-glucosamine to produce the diverse biocompatible polymers needed for the formation of the medical devices of the invention. Such graft or block copolymers can be formed by olefinic compounds, both mono- and di-olefinic compounds, including acrylic acid and esters thereof with saturated alcohols, hydroxyalkyl methacrylate, alkylamino alkmethacrylate, olefin glycols, azo compounds; N-vinyl pyrrolidone, poly(N-vinylpyrrolidone), etc. Reactions covering these copolymers are given in the following for starch: U.S. Pat. No. 3,414,530 shows graft copolymers of a polyalkylene oxide on starch and dextrin polysaccharides. U.S. Pat. No. 3,332,897 describes a process for preparing polysaccharide esters for simultaneously polymerizing and grafting an ethylenically unsaturated monomer onto the polysaccharide, with an acylating agent selected from acetic, propionic or butyric anhydrides or any combination thereof. U.S. Pat. No. 3,935,099 describes the copolymerization of starch and acrylonitrile. The reactions that are carried out with starch, and cellulose, can be carried out with D-glucosamine. By consulting the literature the specific reaction can be found. This diverse family of block and graft copolymers of D-glucosamine and substituted D-glucosamine provide a unique series of polymers for use in medical devices as well as other uses, such as pharmaceuticals and cosmetics, especially the collagen-D-glucosamine and silicone-D-glucosamine.

Another method which has been used successfully with cellulose, and substituted cellulose, e.g. ethyl cellulose, is block copolymerization through mastication; this method may be found useful with the N-acetyl-D-glucosamine block copolymerization with acrylonitrile, acrylamides, and methacrylates. The polymers or polymer and monomer, are subjected to a mechanical stress like that created by ball milling, mastication, or freezing and thawing of aqueous dispersions, the segments resulting from these breaks are polymeric free radicals in which the free radical sites are located at the ends of the segments where the breaks occurred. If this mechanical depolymerization is carried out in the presence of a monomer, copolymerization is initiated by macroradicals, and a block copolymer of poly(N-acetyl-D-glucosamine) may be produced by combinations of macroradicals.

The mastication technique works on monomers containing an olefin, or multi-olefin bond, such as methacrylic acid and its esters, e.g., methyl methacrylate, ethyl methacrylate; vinyl acetate, acrylonitrile, allyl acrylate, or acrylamides and various combinations of these. The methods and procedure for polymerization using mechanical stress are known in the art.

Polyblending whereby free radicals are generated by mechanical shearing is the easiest for the mixing, or grafting of the polymers and monomers discussed here. Free radicals are formed at the ruptured end of the molecules of the polymers, and are caused to initiate the copolymerization of one or more polymerizable compounds, or monomers. The reaction can be aided by the addition of organic peroxides to the reaction mixture.

If the polymer is itself derived from an olefinic compound and the monomer mixed with it is of the same olefinic compound, the product is a homopolymer. If, on the other hand, it is not the same, as in many instances in this invention, the product consists of a mixture of homopolymer and an interpolymer of the graft or block type in which the different types of monomer molecules in their polymerized form are segregated into separate segments of the molecule. These interpolymers are regarded as polymer compounds in which different homopolymeric segments are linked together chemically, i.e., copolymerized.

In order to produce polymeric materials by mechanical mixing of polymer and monomers, the mixture must not be in the form of a fluid solution of the polymer in the monomer, since adequate shearing to initiate polymerization by rupturing polymer molecules cannot occur. The constituents of the polymer-monomer mixture and the relative proportions should be selected so that the mixture is somewhat rubbery at the temperature of mastication, if mastication copolymerization is being utilized.

Other factors which can be varied to assist in the production of polymer/monomer mixtures suitable for use in this invention include temperature and the molecular weight of the polymer. The softening effect on the polymer of an increase in the temperature is sometimes useful in assisting its conversion into a rubbery condition. The higher the molecular weight of the polymer, the wider the range of proportions of monomer or plasticizing solvent that result in the production of a product which can be mechanically transformed into a rubbery mixture. It is understood that crosslinking agents and additional plasticizing agents will determine the final product.

The polymer/monomer mixture may be prepared by allowing the polymer to imbibe the monomer before mastication, this method being applicable to gaseous as well as liquid monomers. Plasticizing solvents may be introduced to aid mixing. It will be appreciated that if the monomer is a solid, e.g. acrylamide, it is necessary either to use a plasticizing solvent in order to give the necessary degree of freedom, or to raise the temperature at which the mixture is free, and can be masticated. In any case it is often convenient to mix the polymer and monomer together when the polymer is in a molten or fluid state. The polymer-monomer or polymer-monomer-plasticizing solvent mixture should preferably be converted into the form of an homogeneous swollen mass before polymerization by mechanical means is initiated in order that a uniform polymerization may be easily accomplished. This may be expedited by stirring or churning the mass in an open mixer and/or by raising the temperature. Increase in temperature is useful with polymer-monomer mixtures which gel at elevated temperature.

The series of polymers includes the following: D-glucosamine and acrylonitrile; D-glucosamine and an acrylamide; D-glucosamine and an acrylic acid or ester, D-glucosamine and a methacrylic acid or ester, D-glucosamine and a protein or polypeptide compound, D-glucosamine and collagen; D-glucosamine and elastin and/or resilin; D-glucosamine and an azo compound, e.g. N-vinyl pyrrolidone; and the chemical families represented by the above compounds. These compounds produce a diverse family of compounds, and whether the specific compound is graft or block polymerized through chain cleavage and free radical formation, or substituted on the side chain through the hydroxyl, or N-acetyl group, they are applicable to the following medical devices and uses:

A. Absorbable polymer alone
   1. Solid products, molded or machined
      a. Orthopedic pins, clamps, screws and plates
      b. Clips (e.g. for use as hemostat)
      c. Staples
      d. Hooks, buttons and snaps
      e. Bone substitute (e.g. mandible prosthesis)
      f. Non-permanent intrauterine devices
      g. Vascular implants or supports
      h. Vertebral discs
      i. Extracorporeal tubing for kidney and heart-lung machines
   2. Fibrillar Products, knitted or woven, including velours
      a. Burn dressings
      b. Hernia patches
      c. Absorbent paper or swabs
      d. Medicated dressings
      e. Facial Substitutes
      f. Gauze, fabric-sheet, felt or sponge for liver hemostasis
      g. Gauze bandages
      h. Dental packs
      i. Surgical sutures
   3. Pharmaceuticals
      a. Dental
      b. Drug
      c. Ophthalmic Any other medical devices which can be used in the body, such as drug release devices, arterial graft or substitutes, bandages for the skin surface, burn dressings (in combination possibly with other polymeric films), two component systems, etc.

Contact lenses are well known in the art and have been used for many years. The lenses are made of several kinds of plastic; silicone rubber poly(2-hydroxyethyl methacrylate), cellulose acetate butyrate, and poly(methyl methacrylate). While these materials are optically satisfactory, their use has some disadvantages. Some are not gas permeable, some will not wet properly, others, e.g., soft lenses, tend to tear easily, and some have low biocompatibility. Accordingly it would be highly desirable to have a family of polymers to form contact lenses which are flexible, optically clear, water wettable, hydrophilic to various degrees, highly permeable to oxygen and carbon dioxide and which in general exhibit a high degree of biocompatibility. The chitin products of this invention fulfill this requirement.

The main disadvantage of known soft of hydrophilic contact lenses is that they have low tensile strength. The average life of a soft lens presently on the market is from six months to one year, and with patient use the lens tears easily. This invention provides materials formed from cellulose or silicone graft copolymers which can have a high tensile strength, thereby overcoming the present disadvantages of soft lenses.

The N-acetyl-D-glucosamine, the substituted and copolymers of N-acetyl-D-glucosamine, all form materials which can be used for contact lenses. The substituted N-acetyl-D-glucosamine of poly(N-acetyl-6-0-carboxymethyl)-D-glucosamine, etc. and even chitin and chitosan 40/60, form clear films with high tensile strength and varying degrees of water absorption, I. Jaffe and H. R. Hepburn, "Observation on Regenerated Chitin Films", J. Material Science, 8(1973)1751–1754, give values on the strength of films of regenerated chitin, from a chitin xanthate dispersion, including a comparison of strength after 30 years storage as $6.3 \times 10^3$ pounds/sq inch.

Contact lenses are usually formed by casting, molding or lathe cutting of plastic buttons. The D-glucosamine (chitin-chitosan 40/60 chitosan-collagen, etc.) can be cast into a contact lens, by dissolving it in a solvent and placing it either in a spin cast mold, or between a male and female die in a cavity, and allowing the solvent to evaporate, by any suitable means. To lathe cut the lenses, the D-glucosamine compound composition is placed in a mold, or device to form it into a sheet or rod form. The sheet is usually about 5/16 inch thick, the rod is formed into ½ inch diameter. The rod or sheet is then cut into what is known in the trade as buttons, buttons are usually cylindrical in shape having dimensions of ½ inch diameter and 5/16 inch thickness. The buttons are mounted on radius cutting lathes, the concave surface is usually cut first, the radius is cut to a predetermined curvature, the radius is polished to remove all lathe marks on the lens. A polishing tool using commercial polishing agents, such as tin oxide, is used to polish the surface, other polishing agents used in the contact lens industry as polishing agents may also be used. After the concave surface has been polished, the semi-finished lens is mounted into an outside cutting lathe, the power radius, or convex, surface is now generated. The convex surface is then polished to remove all lathe marks. The lens is removed from the tool and cut to diameter, and the edge finished. The side surfaces of the lens are subject to a bevel machine to produce a completed lens.

The polymers which can be used to form contact lenses, and particular to such polymers is that they can be prepared with modifiers, plasticizers, and crosslinking agents, are those compositions of D-glucosamine mentioned in this disclosure which are optically clear. It will also be evident that additional modification with N-acetyl-D-glucosamine will be possible and will form contact lenses.

Because of the ability of N-acetyl-glucosamine to act as a wound-healing accelerator, it can find an additional application for patients who have undergone cataract surgery, or any other type of eye surgery to accelerate the healing process. The N-acetyl-glucosamine should be formed into a soft lens material, or polyblended into the carrier polymer to allow for maximum therapeutic effect, although any method is acceptable that will allow for the material to become functional. Since the eye after undergoing surgery is somewhat sensitive, it would be to the patient's advantage to use a carrier which is soft, (chitin-collagen, etc.), or any soft lens material available.

The N-acetyl-glucosamine can be placed into solutions, and ointments for use in the eye, and to act as wetting agents and viscosity builders in contact lens solutions. This will reduce the overwear syndrome experienced with contact lenses. the N-acetyl-D-glucosamine compounds produce excellent viscosity builders and wetting agents for ophthalmic solutions and contact lens solutions. The compositions act as both a wetting agent and viscosity builder, among other things. The viscosity building characteristics, are used in the solution to provide cushioning and corneal comfort, while avoiding stickiness of the eyelid and granulation on the eyelashes. These desirable properties can best be achieved through the use of D-glucosamines as the viscosity building agents and wetting agents, along with the other properties as part of the chemistry of the D-glucosamine compounds.

The use of the polymers of this invention also constitutes a novel composition for use in ophthalmic compositions and preparations. The compositions act as both a wetting agent and viscosity builder, among other things. The viscosity building characteristics are used in the solution to provide cushioning and corneal comfort, while avoiding stickiness of the eyelid and granulation on the eyelashes. These desirable properties can best be achieved through the use of the polymers described in this invention, and the use of said polymers over the current use of hydroxy cellulose compounds.

The essential characteristics of an ideal wetting solution can be summarized as follows:

It should wet thoroughly and spread over the entire surface of the lens;

It should form a film which is sufficiently tenacious so that it will not be washed away during the wearing period of the lens;

It should be so formulated that it can be placed directly into the eye, i.e. it should be non-irritating and non-sensitizing;

It should be a compound so that it will not leave a residue of film on the lenses or the skin around the eye after drying;

It should have a cleaning and antiseptic action and should be self-preserving;

It should not interfere with immersion wetting by the lachrymal fluid;

It should have the proper degree of viscosity for efficient lubrication.

In accordance with the present invention, a contact lens solution made which has all of the above desirable attributes is made containing as an ingredient a N-acetyl-D-glucosamine compound, (i.e. chitosan), since these polymers exhibit the necessary properties for use in contact lens solutions.

As specific examples of ophthalmic solutions, the following examples are given only as an illustration:

EXAMPLES

Artificial tears consisting of a sterile solution of 1.8% to 3.4% of a D-glucosamine, 0.5% polysorbate 80 (polyoxyethylene(20) sorbitan monooleate), in an isotonic solution preserved with 0.5% chlorobutanol. It is used to counteract dryness in the absence of natural tears or from irritation due to excessive wearing of contact lenses, 2 or 3 drops are placed in the eye several times a day.

Contact lens cleaning solution: Surfactant 3.5%, thimerosal 0.004% disodium edelate 0.2%, D-glucosamine 0.8%, distilled water. The cleaner is used to clean hard and gas permeable contact lenses. Soaking solution: D-glucosamine 1.2%, thimerosal 0.001%, chlorhexidine 0.005%, disodium edelate 0.1%, isotonic solution of sodium chloride, sodium borate, boric acid to ph 7.2 and water.

Anti-inflammatory ointment; polymyxin B sulfate 5,000 units/gr., zinc bacitracin 400 units/gr., neomycin sulfate 5 mg/gr., hydrocortisone 10 mg/gr., D-glucosamine 18.7%/gr., white petroleum remainder.

The D-glucosamines can also be used as carriers for all other ophthalmic pharmaceuticals, such as drugs which produce mydriasis and cyclopegis, and phenylephrine, adrenaline, cocaine, atropine, etc. The use of glaucoma treatment agents can be combined with the D-glucosamine to increase the viscosity and therapeutic effectiveness of the drugs such as epinephrine.

The following examples are given to illustrate the methods of grafting onto chitin and chitosan, and in no way are to imply any limitations on the invention.

EXAMPLE

A 26 oz bottle was charged with 10 gms CTC organics Chitin Flake (95.1% nonvolatile), and 190 gms deionized water. Nitrogen was bubbled through the mix for 30 minutes and the bottle was sealed overnight. A 0.1 M cerium solution was prepared: 5.48 gms (NH$_4$)$_2$Ce(NO$_3$)$_6$ qs 0.25 N HNO$_3$ to 100 ml total. A 12 ml quantity of cerium solution was added to the bottle, the bottle was flushed with nitrogen, sealed and agitated for 10 minutes. The bottle was opened, 5 gms of methacrylic acid was added, the bottle was flushed with nitrogen, sealed, and tumbled 3 hours in a 35° C. polymerization oven to batch graft the acrylic acid to the Chitin. The bottle contents were washed into a weighed dish, evaporated in an air draft for two days, and dried in a vacuum oven to determine the yield. The Chitin and Chitosan flakes were also dried to determine the volatile content. The % of monomer was calculated as follows:

% Monomer polymerized = Final dry weight-weight of dry basis Chitosan/weight of monomer charged.

A similar procedure was followed for the methyl methacrylate graft, Chitosan and MMA were utilized: 10 gms CTC Organics Chitosan flake, 190 gms deionized water, 12 ml 0.1 M Cerium Solution 5 gms R&H Methyl Methacrylate. The % of monomer polymerized is as follows: Chitin-methacrylic acid 26.8. Insoluble in DMF, sodium/hydroxide solution.

Chitosan-Methyl methacrylate 18.7, insoluble in dichloroethane, in 2% acetic acid, the polymer is largely soluble but a quantity of white material slowly settles out. Castings were prepared by dissolving Chitosan (4% solids) and Croda Inc. Crotein SPC Collagen (8% solids) in 2% acetic acid, mixing the solutions (50 Chitosan/50 Crotein solids) and drying down at 60° C. with a 4 hour/100° C. post heating to encourage interaction. Filtered Chitosan solution was used.

The above examples illustrate the process of utilizing ceric salts, such as the ceric ammonium nitrate to initiate free radical grafting copolymerization on chitin and chitosan.

These examples are merely a simplified illustration and are not to be understood as limiting the scope and underlying principles of this part of the invention in any way. Which is the utilization of D-glucosamine compounds in all opthalmic preparations, either by themselves, or in conjunction with other chemicals, and known preparations and compounds.

The chitin derivatives contemplated for incorporation into opthalmic solutions and ointments are also materials formed with pharmaceutically acceptable radicals and esters or salts with pharmaceutically acceptable acids. However, in certain opthalmic application of ointments and solutions it may be preferred to use natural chitin or chitosan.

With some though it is evident that permutations and combinations among the various polymers and copolymers presented here can be found. It is also apparent that changes and modifications may be made without departing from the invention in its broader aspects. The aim of the appended claims, therefore is to cover all such changes and modifications as fall within the true spirit and scope of the invention.

What is claimed is:

1. A polymeric composition formed from D-glucosamine or derivatives thereof selected from the group consisting of N-acetyl-D-glucosamine, substituted N-acetyl-D-glucosamine, derivatives of N-acetyl-D-glucosamine and graft and block polymers of N-acetyl-D-glucosamine, and a compound selected from the group consisting of a silicone, collagen, acrylonitrile, acrylamide, methacrylate acids and esters, alkylaminoalkyl methacrylate and hydroxyalkyl methacrylate and pyrrolidone and derivatives of pyrrolidone.

2. A composition according to claim 1 consisting of a D-glucosamine or derivative thereof and silicone.

3. A composition according to claim 1 consisting of a D-glucosamine or derivative thereof and collagen.

4. A composition according to claim 1 consisting of a D-glucosamine or derivative thereof and acrylonitrile.

5. A composition according to claim 1 consisting of a D-glucosamine or derivative thereof and acrylamide.

6. A composition according to claim 1 consisting of a D-glucosamine or derivative thereof and methacrylate acids and esters, alkylaminoalkyl methacrylate and hydroxyalkyl methacrylate.

7. A composition according to claim 1 consisting of a D-glucosamine or derivative thereof and pyrrolidone or a derivative thereof.

* * * * *